(12) United States Patent
Perkins et al.

(10) Patent No.: US 12,741,078 B2
(45) Date of Patent: Sep. 22, 2026

(54) OCCLUSION DETECTION IN VACUUM-BASED OPHTHALMIC SURGICAL SYSTEMS

(71) Applicant: Bausch + Lomb Ireland Limtied, Dublin (IE)

(72) Inventors: James T. Perkins, St. Peters, MO (US); Logan C. Kluesner, St. Charles, MO (US); David W. Hertweck, Valley Park, MO (US)

(73) Assignee: Bausch + Lomb Ireland Limited, Dublin (IE)

( * ) Notice: Subject to any disclaimer, the term of this patent is extended or adjusted under 35 U.S.C. 154(b) by 430 days.

(21) Appl. No.: 18/378,016

(22) Filed: Oct. 9, 2023

(65) Prior Publication Data

US 2024/0148955 A1 May 9, 2024

Related U.S. Application Data

(60) Provisional application No. 63/415,098, filed on Oct. 11, 2022.

(51) Int. Cl.
*A61M 1/00* (2006.01)
*A61F 9/007* (2006.01)

(52) U.S. Cl.
CPC ......... *A61M 1/774* (2021.05); *A61F 9/00736* (2013.01); *A61M 1/73* (2021.05);
(Continued)

(58) Field of Classification Search
CPC ............ A61M 1/73; A61M 1/77; A61M 1/74; A61M 1/774; A61M 2205/3331;
(Continued)

(56) References Cited

U.S. PATENT DOCUMENTS 7,785,316 B2 8/2010 Claus et al.
8,425,452 B2 4/2013 Claus et al.
(Continued)

FOREIGN PATENT DOCUMENTS

WO 2016150754 A1 9/2016
WO 2019069201 A1 4/2019
WO 2021124171 A1 6/2021

OTHER PUBLICATIONS

International Search Report and Written Opinion of the International Searching Authority for Internation Application No. PCT/US2023/034810 dated Feb. 1, 2024, 14 pages.
(Continued)

*Primary Examiner* — Kyle Robert Thomas
(74) *Attorney, Agent, or Firm* — Harness, Dickey & Pierce, P.L.C.

(57) ABSTRACT

Occlusion detection in a vacuum-based system for ophthalmic surgery includes a handpiece and aspiration and irrigation subsystems. The aspiration subsystem includes an aspiration line coupled to a handpiece, an aspiration pressure transducer, and a vacuum-based aspiration pump. The irrigation subsystem includes an irrigation line coupled to an irrigation source having an irrigation fluid, a handpiece, an irrigation pressure transducer, and a positive displacement pump. The system also includes a processor coupled to the positive displacement pump and a memory coupled to the processor. The memory includes executable instructions that cause the processor to determine a flow rate of irrigation fluid through the irrigation line, based on a rotation rate of the positive displacement pump, and provide an occlusion warning when the flow rate is below a threshold level and a vacuum is being commanded.

20 Claims, 2 Drawing Sheets

Figure 1:
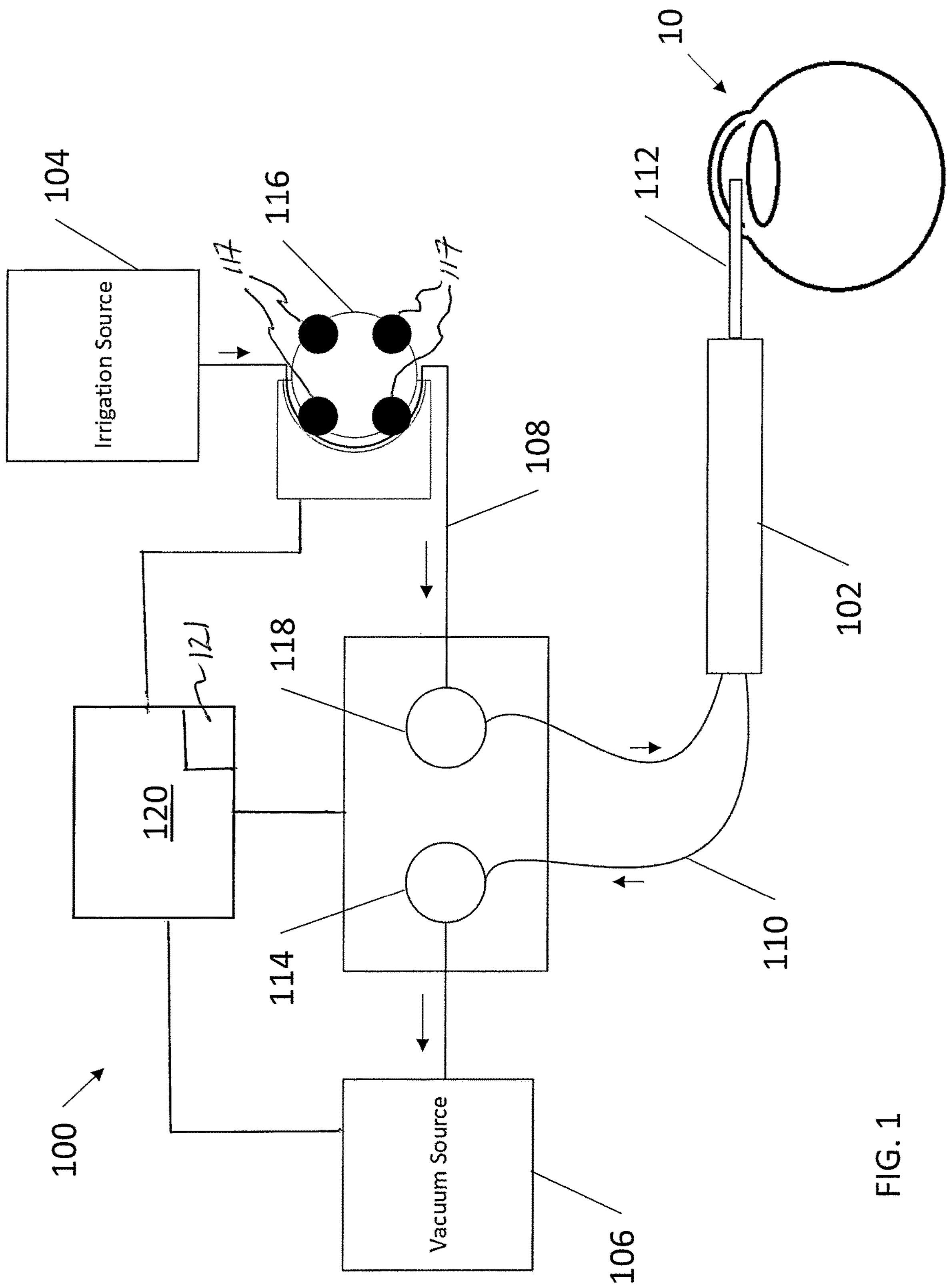

(52) U.S. Cl.
CPC ....... *A61M 1/74* (2021.05); *A61M 2205/3334* (2013.01); *A61M 2205/3341* (2013.01); *A61M 2205/3355* (2013.01); *A61M 2205/3365* (2013.01); *A61M 2210/0612* (2013.01)

(58) Field of Classification Search
CPC .. A61M 2205/3334; A61M 2205/3341; A61M 2205/3344; A61M 2205/3365; A61M 2210/0612
See application file for complete search history.

(56) References Cited

U.S. PATENT DOCUMENTS

| | | | | |
|---|---|---|---|---|
| 10,342,701 | B2 * | 7/2019 | Rockley .................. | A61M 1/74 |
| 2002/0019607 | A1 * | 2/2002 | Bui ..................... | A61F 9/00745 604/67 |
| 2016/0220751 | A1 * | 8/2016 | Mallough ............... | A61M 1/72 |
| 2017/0136159 | A1 | 5/2017 | Mallough | |
| 2019/0099526 | A1 * | 4/2019 | Hajishah ............. | A61F 9/00745 |
| 2019/0099547 | A1 | 4/2019 | Mehta et al. | |
| 2021/0290836 | A1 | 9/2021 | Köppel | |

OTHER PUBLICATIONS

International Preliminary Report on Patentability for International Application No. PCT/US2023/034810 dated Apr. 15, 2025, 11 pages.

Communication pursuant to Rules 161 and 162 EPC dated May 20, 2025 received by the European Patent Office related to European Application No. 23801974.9, 3 pages.

* cited by examiner

200

OCCLUSION DETECTION IN VACUUM-BASED OPHTHALMIC SURGICAL SYSTEMS

FIELD

The present disclosure generally relates to vacuum-based ophthalmic surgical systems, and more particularly, to vacuum-based ophthalmic surgical systems having a positive displacement irrigation pump with occlusion detection.

BACKGROUND

This section provides background information related to the present disclosure which is not necessarily prior art.

Ophthalmic surgery often involves cutting away or emulsifying tissues that need to be removed from the eye, such as in cataract surgery. One known technique is phacoemulsification. This technique involves using high frequency ultrasound energy transmitted through a handpiece into a phacoemulsification needle tip to emulsify the affected tissue. Generally, the handpiece is coupled to an irrigation source (e.g., an elevated bottle of saline fluid, etc.) and an aspiration pump. To maintain the eye in a pressurized condition during surgery and to aid in the aspiration of the emulsified tissue, saline fluid is introduced into the eye from the irrigation source through the handpiece. As the tissue is emulsified by the phacoemulsification needle, the saline fluid, as well as the emulsified tissue, is aspirated from the eye through the handpiece by the aspiration pump.

One type of aspiration pump is a vacuum-based pump such as, for example, a venturi pump. In operation, a vacuum-based pump indirectly controls fluid flow by controlling vacuum. Vacuum-based systems generally pull the fluid through the aspiration line by vacuum (e.g., rather than aspiration with a positive displacement pump, e.g. a peristaltic pump). In such a system, as the vacuum increases, aspiration flow rate likewise increases. For example, a vacuum-based pump creates a lower pressure compared to the intraocular pressure (IOP), in a drainage cassette, that causes the fluid to flow from the eye and into the cassette. Another type of aspiration pump is a positive displacement pump, typically a peristaltic pump, which aspirates fluid through the aspiration line via a series of rollers periodically pinching a tube. The expansion of the tube, after contraction creates a vacuum/suction that draws the fluid through the tube. By knowing the tube materials, the tube inner diameter, the number of rollers pinching the tube, and the rotation rate of the rollers, one can calculate a flow rate of fluid through the tube.

During normal surgical conditions, the flow rate of the saline fluid irrigated into the eye roughly matches the flow rate of the emulsified tissue and saline fluid aspirated from the eye, resulting in a stable volume of liquid in the anterior chamber of the eye. Occasionally, the handpiece (e.g., the phaco tip, etc.) becomes occluded with aspirated material during surgery, which interrupts the aspiration flow and in turn, causes interruption in the irrigation flow and/or an increase in IOP.

After the material occluding the phaco tip clears, an effect referred to as post-occlusion surge can occur. Post-occlusion surge happens when fluid rushes into the aspiration port after the material occluding the phaco tip clears, filling the vacuum in the tubing and causing a subsequent drop in intraocular pressure, which can lead to potential surgical complications. For example, post-occlusion surge can cause the anterior chamber to shallow or cause the iris or posterior capsule to move toward the phacoemulsification tip, increasing the potential risk of posterior capsule rupture or iris trauma.

Conventionally, there has been one method for detecting occlusion during ophthalmic surgery and this method is only available in systems using a positive displacement pump for the aspiration flow (e.g., as opposed to a vacuum-based pump, etc.). In such systems, if a maximum vacuum setting is reached, the aspiration peristaltic pump stops and it is assumed that the handpiece is occluded. When this happens, an occlusion warning may be provided to the surgeon. Using this method, the surgeon can choose to stop providing power to the handpiece and minimize the chance of surgical complications. In contrast, vacuum-based ophthalmic surgical systems only control the vacuum level and simply maintain a set or commanded vacuum level in the aspiration path. Because flow through the system is based on the vacuum level, the resulting flow rate is variable and unmonitored, such that vacuum-based systems are generally unable to detect when occlusion occurs.

SUMMARY

This section provides a general summary of the disclosure, and is not a comprehensive disclosure of its full scope or all of its features.

Example embodiments of the present disclosure generally relate to vacuum-based systems for ophthalmic surgery that include occlusion detection. In one example embodiment, the system includes a processor and a memory coupled to the processor, a handpiece coupled to the processor, an aspiration subsystem operatively coupled to the handpiece, and an irrigation subsystem operatively coupled to the handpiece. The aspiration subsystem includes a vacuum-based aspiration pump, an aspiration line coupled to the handpiece and the vacuum-based aspiration pump, and an aspiration pressure transducer for sensing a pressure within the aspiration line operatively coupled to the aspiration line and the processor. The irrigation subsystem includes an irrigation source having an irrigation fluid, an irrigation line coupled to the handpiece and the irrigation source, a positive displacement pump operatively coupled to the irrigation line between the irrigation source and the handpiece, the positive displacement pump operatively coupled to the processor, and a pressure transducer coupled to the irrigation line for sensing an irrigation pressure within the irrigation line, the pressure transducer operatively coupled to the processor. The memory comprises executable instructions that, when executed by the processor, cause the processor to determine a flow rate of the irrigation fluid through the irrigation line, based on at least a rotation rate of the positive displacement pump and the pressure sensed by the pressure transducer, determine if a vacuum is being commanded by the vacuum-based aspiration pump, and provide an occlusion warning to a user when an irrigation flow rate is below a threshold level and the vacuum is being commanded. In another example embodiment, a method of providing occlusion detection in a vacuum-based ophthalmic surgical system is provided. The method includes receiving, by a computing device, operational data from a positive displacement pump and pressure data from an irrigation transducer. Both the positive displacement pump and the irrigation transducer are operatively coupled to an irrigation line The irrigation line also connects a handpiece to a source of irrigation fluid. The method further includes determining, by the computing device, whether a vacuum is being commanded of a vacuum-based aspiration pump coupled to the handpiece, calculating, by the computing device, an irrigation flow rate of the irrigation fluid through the irrigation line, based on the operational data and the pressure data, comparing, by the computing device, the calculated irrigation flow rate to a threshold, and providing to a user, by the computing device, an occlusion warning when the irrigation flow rate fails to satisfy the threshold and the vacuum is being commanded.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 2:
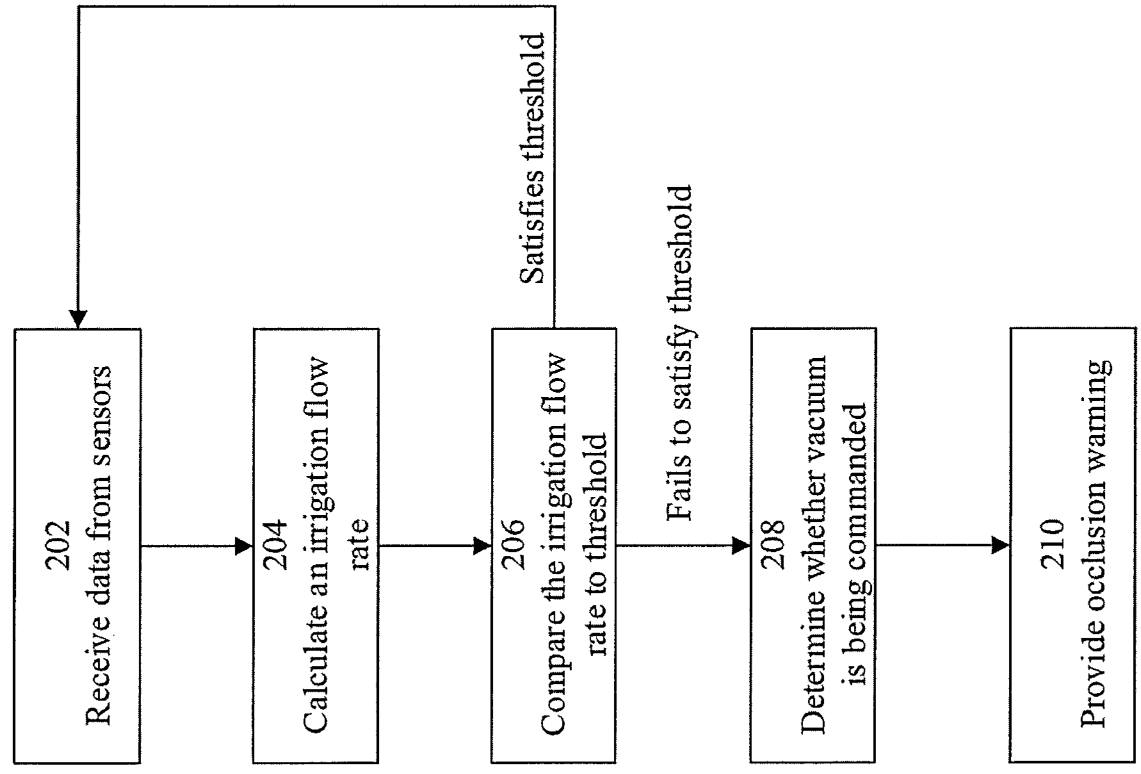

FIG. 1 is a block diagram of an example embodiment of a vacuum-based ophthalmic surgical system having occlusion detection; and FIG. 2 is a block diagram of a method detecting occlusion in a vacuum-based ophthalmic surgical system.

Corresponding reference numerals indicate corresponding parts throughout the several views of the drawings.

DETAILED DESCRIPTION

Example embodiments of the present disclosure generally relate to vacuum-based systems for ophthalmic surgery. Current vacuum-based ophthalmic surgical systems utilize a vacuum-based pump to aspirate fluid and other materials out of the eye through an aspiration line, while fluid supplied from an irrigation source is irrigated into the eye through an irrigation line. In such a system, the pressure within the irrigation line (and resulting irrigation flow) is independent of the vacuum created by the vacuum-based pump and generally occlusion detection is unavailable for vacuum systems. Uniquely, the systems of the present disclosure integrate an irrigation pump and a pressure transducer on the irrigation side (e.g., operatively coupled to the irrigation line, etc.) to create a flow of irrigation fluid at a set irrigation pressure into the eye that is independent of and separate from the aspiration flow of fluid out of the eye created by the vacuum-based pump. In this way, aspiration flow is controlled by the vacuum-based pump, and the irrigation flow is independently controlled by the positive displacement pump. By placing a positive displacement pump and a pressure transducer in the irrigation path, a set irrigation pressure can be maintained, regardless of the flow rate of the saline fluid from the eye (i.e., aspiration). The pressure on the irrigation side may be monitored (e.g., by a pressure transducer, etc.), as well as operation conditions of the pump motion (e.g., rotation rate/speed (rpm), etc.), to determine an irrigation flow rate. If the flow rate drops below a threshold while the surgeon is commanding vacuum (e.g., via a foot pedal, console input, etc.), it is determined that an occlusion is likely occurring, and an occlusion warning is provided to the surgeon. By introducing a positive displacement pump on the irrigation side, occlusion detection can be provided in vacuum-based systems.

Example embodiments will now be described more fully with reference to the accompanying drawings. The description and specific examples included herein are intended for purposes of illustration only and are not intended to limit the scope of the present disclosure.

FIG. 1 illustrates an example embodiment of an ophthalmic surgical system 100 including one or more aspects of the present disclosure. In the illustrated embodiment, the system 100 generally includes a handpiece 102 (e.g., a phacoemulsification handpiece, etc.), an irrigation source 104 and a vacuum source 106. On the irrigation side of the system 100 (broadly, an irrigation subsystem), the irrigation source 104 (e.g., an elevated bottle/bag of a saline fluid, etc.) is in fluid communication with the handpiece 102 by way of an irrigation line 108. The irrigation source 104 is configured to supply saline fluid (broadly, irrigation fluid) for the system 100. The irrigation source 104 is coupled to a first end of the irrigation line 108 and the handpiece 102 is connected to a second end of the irrigation line 108. The irrigation subsystem also includes a positive displacement pump 116 operatively coupled to the irrigation line 108 between the irrigation source 104 and the handpiece 102, and a pressure transducer 118 coupled to the irrigation line 108 for sensing an irrigation pressure within the irrigation line 108. On the aspiration side of the system 100 (broadly, an aspiration subsystem), the vacuum source 106 (e.g., a vacuum-based aspiration pump, etc.) is in fluid communication with the handpiece 102 by way of an aspiration line 110, and an aspiration pressure transducer 114 for sensing a pressure within the aspiration line 110. The vacuum source 106 is configured to move fluid through the system 100 (e.g., draw fluid out of the eye 10 through the aspiration line 110, etc.) by creating vacuum/suction. The vacuum source 106 is coupled to a first end of the irrigation line 110 and the handpiece 102 is connected to a second end of the aspiration line 110 and the aspiration pressure transducer is placed in communication with aspiration line 110 between the vacuum source 106 and the handpiece 102.

The handpiece 102 includes a phacoemulsification needle 112 having a tip configured for insertion into an eye 10 during surgery. The handpiece 102 also includes a vibration source (not shown) configured to sonically or ultrasonically vibrate the needle 112. The needle 112, when vibrated by the vibration source (e.g., a piezoelectric stack, etc.), is configured to emulsify tissue within the eye 10. To maintain pressure within the eye and to aid in aspiration of emulsified material from the eye 10, saline fluid from the irrigation source 104 is irrigated into the eye 10 through one or more ports of a sleeve (unshown) surrounding the needle 112. The saline fluid, along with emulsified material, is aspirated out of the eye 10 by the vacuum source 106.

The vacuum source 106 includes a vacuum-based pump, for example, a venturi pump, etc. The vacuum source 106 is configured to create vacuum which draws fluid from the eye 10 through the aspiration line 110 to a drainage cassette (not shown) (broadly, aspiration flow). To monitor the vacuum level within the aspiration line 110, the system 100 also includes an aspiration pressure transducer 114 in communication with the aspiration line 110. The aspiration pressure transducer 114 is used in connection with setting the desired vacuum level of the vacuum source 106.

As part of the irrigation subsystem, the system 100 also includes components for detecting occlusion. In particular, the system 100 includes the positive displacement pump 116 for creating a flow of fluid through the irrigation line 108 (broadly, irrigation flow or flow rate) and a pressure transducer 118 for monitoring the pressure within the irrigation line 108. The pump 116 is coupled to the irrigation line 108 between the irrigation source 104 and the handpiece 102. The pressure transducer 118 is coupled to the irrigation line 108 between the pump 116 and the handpiece 102. In the illustrated embodiment, the pump 116 is a peristaltic pump.

However, in other embodiments, other positive displacement pumps may be used (e.g., rotary, reciprocating, linear, etc.). In the system 100, settings for the irrigation side of the system 100, such as the infusion pressure (e.g., as detected by the pressure transducer 118, etc.), are set independently from settings for the aspiration side of the system 100 (e.g., a vacuum setting of the vacuum source 106, etc.). For example, irrigation flow in the irrigation line 108 is controlled independently and separately from aspiration flow in the aspiration line 110.

A processor/computing device 120 (e.g., a processor, a controller, etc.) is operatively coupled to the handpiece 102 (not shown), the vacuum source 106, the aspiration pressure transducer 114, the pump 116, and the irrigation pressure transducer 118, as shown. The processor 120 is typically housed in a surgical console that may also contain the vacuum source 106 and the pump 116 and may also hold transducers 114, 118. The computing device 120 is configured (e.g., by executable instructions included in a memory 121, etc.) to implement settings for the aspiration subsystem (e.g., vacuum level, etc.) and the irrigation subsystem (e.g., set an irrigation pressure of the fluid within the irrigation line 108, etc.). For a given irrigation line material and inner diameter and a number of rollers 117 and a rotation radius of the rollers 117 of pump 116 a known volume of fluid is aspirated each time a roller pinches the line 108 and then retracts from the pinch position and can be obtained from the pump manufacturer or empirically obtained through testing. From this known information stored in memory 121 and sensing the pressure and the speed of rotation of the rollers 117 an irrigation flow rate may be calculated and monitored. The computing device 120 is also configured to control functionality of the components of the system 100 (e.g., the handpiece 102 (connection not shown), the vacuum source 106, etc.), for example, based on input(s) received from a foot pedal (not shown) or otherwise. The computing device 120 is also configured to detect occlusion within the system 100, as will be described in more detail below. It should be appreciated that while one computing device 120 is shown in the illustrated embodiment, the configurations of the computing device 120 may be implemented in a distributed system by one or more computing devices in other embodiments.

When the positive displacement pump 116 is in an operational state (e.g., turned on, etc.), irrigation fluid is pulled from irrigation source 104 and pushed through the irrigation line 108 by the pump 116 and the fluid flows through the handpiece 102 and into the eye 10. And, when the vacuum source 106 is in an operational state (e.g., when vacuum is commanded by a surgeon via the foot pedal or otherwise, etc.), the aspiration fluid is drawn out of the eye 10 through the handpiece 102 and flows through the aspiration line 110 towards the drainage cassette (unshown). When an occlusion occurs at the handpiece 102 (e.g., material blocks the tip of the needle 112, etc.), fluid is no longer able to flow through the aspiration line 108, out of the eye 10. This results in a decreased flow rate in the irrigation subsystem because an increase in irrigation pressure will be sensed at transducer 118 and detected by processor 120, which in turn, causes the rotation rate of the rollers 117 of peristaltic pump 116 to decrease to maintain a preset irrigation pressure of the fluid within the irrigation line 108 (e.g., as measured by the pressure transducer 118, etc.). During operation of the system 100, the computing device 120 is configured to monitor and calculate the irrigation flow rate based on the pressure and the pump speed. After the irrigation flow rate is calculated, the computing device 120 is configured to compare the flow rate to a threshold level (e.g., a predefined flow rate, a level set some amount above the preset flow rate, etc.). If the positive displacement pump is other than the example peristaltic pump the speed of the pump may be a speed analogous to the rotation rate of the rollers, such as a rotary speed of a scroll, vane, lobe pump or a reciprocating speed of a piston or plunger of a linear pump.

When the irrigation flow rate drops below the threshold level and a vacuum is being commanded by processor 120, it may be assumed that the handpiece 102, or more specifically, the needle 112, is occluded and an occlusion warning is provided by the computing device 120 to the surgeon. The warnings may be audible sounds, a synthesized voice, a light, a tactile signal (vibration, etc.) and/or an icon on a display. Further, because the irrigation flow rate will also decrease temporarily when aspiration (e.g., vacuum, etc.) is no longer being commanded, the computing device 120 is configured to provide an occlusion warning only when aspiration is being commanded and the irrigation flow rate drops below the threshold level. This prevents an occlusion warning from being provided in scenarios when the irrigation flow rate is low for other reasons, such as when the system 100 is being turned off and vacuum is not being commanded. Based on the occlusion warning, the surgeon may take various actions to mitigate post-occlusion surge and/or prevent surgical complications arising from post-occlusion surge, for example, by removing power from the handpiece 102 to stop vibration of the needle 112 and/or to stop commanding vacuum.

FIG. 2 illustrates an example method for use in detecting occlusion in the system 100 and providing an occlusion warning to users of the system 100. The method 200 is described as implemented in the computing device 120, and more generally in the system 100. However, it should be understood that the method 200 is not limited to this configuration of the system 100, as the method 200 may be implemented, at least in part, in other computing devices or systems. As such, the methods herein should not be understood to be limited to the exemplary method 200.

At the outset in the method 200, the computing device 120 receives data from the sensors, at 202. In particular, the computing device 120 receives operational data from the pump 116 (e.g., a speed of the pump 116, etc.) and a pressure reading from the pressure transducer 118 (e.g., a pressure of the irrigation line 108, etc.). It should be appreciated that the computing device 120 may receive additional data from other sensors and/or inputs, including without limitation data from the aspiration pressure transducer 114, an input from the foot pedal (not shown), or other input devices, etc. The computing device 120 may receive the data on a continuous basis, periodic, and/or intermittent basis from the different components of the system 100, depending on the requirements and capabilities of system 100.

After receiving the operational and pressure data, the computing device 120 calculates, at 204, a flow rate of the saline fluid through the irrigation line 108 based on the operational data of the pump 116 and the pressure reading from the pressure transducer 118. The computing device 120 compares, at 206, the calculated irrigation flow rate to a threshold. This comparison is indicative of whether or not an occlusion has occurred, based on a decreased flow rate on the irrigation side. If the calculated flow rate satisfies the threshold (e.g., the flow rate is at or above the threshold, etc.), the computing device 120 continues monitoring for occlusion by repeating steps 202-206 of the method 200. The threshold is set at a low enough flow rate to account for normal fluctuations in flow rate during surgery to minimize false occlusion warnings to a user.

If the calculated flow rate fails to satisfy the threshold (e.g., the flow rate is below the threshold, etc.), this may be indicative that the system 100 is occluded. In response, the computing device 120 determines, at 208, whether vacuum is being commanded on the aspiration side of the system 100 (e.g., based on an input received from a foot pedal or other input device, as part of step 202, etc.). In particular, if the flow rate on the irrigation side drops below the threshold level and vacuum is being commanded on the aspiration side by the operator of the system 100 (e.g., a surgeon, etc.), this indicates that occlusion has occurred. In some embodiments, the computing device 120 determines whether vacuum is being commanded at 208, prior to calculating the flow rate at 204 and/or comparing the flow rate to the threshold at 206.

Thus, if the irrigation flow rate drops (e.g., based on the comparison of the calculated flow rate to the threshold, etc.) while vacuum is being commanded, the computing device 120 provides, at 210, an occlusion warning or notification to a user of the system 100 (e.g., a surgeon, etc.). In some embodiments, the occlusion warning is a visual, auditory, and/or a tactile indicator. After the occlusion warning is provided by the computing device 120, actions may be taken by the user to mitigate post-occlusion surge and/or prevent surgical complications arising from post-occlusion surge.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Specific dimensions, specific materials, and/or specific shapes disclosed herein are example in nature and do not limit the scope of the present disclosure. The disclosure herein of particular values and particular ranges of values for given parameters are not exclusive of other values and ranges of values that may be useful in one or more of the examples disclosed herein. Moreover, it is envisioned that any two particular values for a specific parameter stated herein may define the endpoints of a range of values that may be suitable for the given parameter (i.e., the disclosure of a first value and a second value for a given parameter can be interpreted as disclosing that any value between the first and second values could also be employed for the given parameter). For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" as well as the phrase "at least one of" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper", "lower" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the present disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the present disclosure, and all such modifications are intended to be included within the scope of the present disclosure.

What is claimed is:

1. An ophthalmic surgery system comprising:

a processor and a memory coupled to the processor;

an aspiration subsystem including:

an aspiration pump configured to be controlled by the processor, an aspiration line coupled between a handpiece and the aspiration pump, and an aspiration pressure transducer for sensing a pressure within the aspiration line and operatively coupled to the aspiration line and the processor;

an irrigation subsystem including:

an irrigation line configured to be coupled to the handpiece and an irrigation source, a positive displacement pump operatively coupled to the irrigation line to pump an irrigation fluid through the irrigation line, the positive displacement pump configured to be controlled by the processor, and an irrigation pressure transducer coupled to the irrigation line configured to sense an irrigation pressure within the irrigation line, the irrigation pressure transducer configured to transmit irrigation pressure data to the processor; and wherein the memory comprises executable instructions that, when executed by the processor, cause the processor to:

determine a flow rate of the irrigation fluid through the irrigation line, determine if the aspiration pump is commanded to generate a vacuum, and provide an occlusion warning to a user when the determined irrigation flow rate is below a threshold level and the generation of the vacuum is being commanded.

2. The system of claim 1, further comprising:

the handpiece operatively configured to be connected to the processor; and the irrigation source having the irrigation fluid.

3. The system of claim 1, wherein the determination of the flow rate is based on at least a rotation rate of the positive displacement pump and the pressure sensed by the irrigation pressure transducer.

4. The system of claim 1, further comprising:

a user input operatively coupled to the processor that is configured to executable instructions to cause the processor to provide the occlusion warning when the flow rate is below the threshold level and the user input is commanding the vacuum from the aspiration pump.

5. An ophthalmic surgery system comprising:

a processor and a memory coupled to the processor;

a handpiece operatively connected to the processor;

an aspiration subsystem including:

a vacuum-based aspiration pump operatively connected to the processor, an aspiration line coupled between the handpiece and the vacuum-based aspiration pump, and an aspiration pressure transducer for sensing a pressure within the aspiration line and operatively coupled to the aspiration line and the processor;

an irrigation subsystem including:

an irrigation source having an irrigation fluid, an irrigation line coupled to the handpiece and the irrigation source, a positive displacement pump operatively coupled to the irrigation line between the irrigation source and the handpiece, the positive displacement pump operatively coupled to the processor, and an irrigation pressure transducer coupled to the irrigation line for sensing an irrigation pressure within the irrigation line, the irrigation pressure transducer operatively coupled to the processor; and wherein the memory comprises executable instructions that, when executed by the processor, cause the processor to:

determine a flow rate of the irrigation fluid through the irrigation line, based on at least a rotation rate of the positive displacement pump and the pressure sensed by the irrigation pressure transducer, determine if a vacuum is being commanded by the vacuum-based aspiration pump, and provide an occlusion warning to a user when the determined flow rate is below a threshold level and the vacuum is being commanded.

6. The system of claim 5, further comprising a foot pedal operatively coupled to the processor, wherein the memory further comprises executable instructions that, when executed by the processor, cause the processor to provide the occlusion warning when the infusion determined flow rate is below the threshold level and the foot pedal is commanding vacuum from the vacuum-based aspiration pump via the processor.

7. The system of claim 6, wherein the memory further comprises executable instructions that, when executed by the processor, cause the processor to provide the occlusion warning based on a sensed increase in pressure at the irrigation pressure transducer.

8. The system of claim 5, wherein the positive displacement pump is a peristaltic pump.

9. The system of claim 5, wherein the positive displacement pump is one of a rotary pump, a reciprocating pump, or a linear pump.

10. The system of claim 5, further comprising:

a needle extending from the handpiece to be inserted in an eye.

11. The system of claim 5, further comprising:

a warning system configured to provide the warning to the user.

12. The system of claim 11, wherein the warning system provides the warning as at least one of an audible sound, a synthesized voice, a light, a tactile signal, or an icon on a display.

13. The system of claim 5, wherein the memory further comprises executable instructions that, when executed by the processor, cause the processor to provide the occlusion warning based on a sensed increase in pressure at the irrigation pressure transducer.

14. A method of providing occlusion detection in a vacuum-based ophthalmic surgical system, the method comprising:

receiving, by a computing device, operational data from a positive displacement pump and pressure data from an irrigation pressure transducer both operatively coupled to an irrigation line, wherein the irrigation line connects a handpiece to a source of irrigation fluid;

determining, by the computing device, whether vacuum is being commanded, by a user input, of a vacuum-based aspiration pump coupled to the handpiece;

calculating, by the computing device, a flow rate of the irrigation fluid through the irrigation line, based on the operational data and the pressure data;

comparing, by the computing device, the calculated flow rate to a threshold; and providing by the computing device, an occlusion warning only when the calculated flow rate is below the threshold and the vacuum is being commanded.

15. The method of claim 14, wherein the operational data includes a rotation rate of the positive displacement pump.

16. The method of claim 15, wherein providing the occlusion warning includes providing the occlusion warning only when the flow rate is below the threshold and the vacuum is being commanded.

17. The method of claim 15, wherein determining, by the computing device, whether vacuum is being commanded of a vacuum-based aspiration pump includes receiving an input from a foot pedal.

18. The method of claim 14, wherein providing the occlusion warning includes providing as the warning as at least one of an audible sound, a synthesized voice, a light, a tactile signal, or an icon on a display.

19. The method of claim 14, further comprising:

providing the computing device with a processor configured to execute instructions.

20. The method of claim 14, wherein receiving, by the computing device, operational data from the positive displacement pump and pressure data from the irrigation pressure transducer includes receiving the operation data and pressure data on at least one of a continuous basis, a periodic, or an intermittent basis.

* * * * *